United States Patent [19]
Dinkel

[11] 4,370,481
[45] Jan. 25, 1983

[54] PROCESS FOR THE PRODUCTION OF 3-PICOLINE

[75] Inventor: Rolf Dinkel, Münchenstein, Switzerland

[73] Assignee: Lonza Ltd., Gampel, Switzerland

[21] Appl. No.: 357,626

[22] Filed: Mar. 12, 1982

[30] Foreign Application Priority Data

Mar. 18, 1981 [CH] Switzerland .......................... 1836/81

[51] Int. Cl.$^3$ .................. C07D 213/08; C07D 213/10
[52] U.S. Cl. .................................................. 546/251
[58] Field of Search ......................... 546/251

[56] References Cited

FOREIGN PATENT DOCUMENTS 1193841  5/1970  United Kingdom ................ 546/251

Primary Examiner—Robert T. Bond
Attorney, Agent, or Firm—Fisher, Christen & Sabol

[57] ABSTRACT

Process for the production of 3-picoline. A first educt consisting of acetaldehyde and/or acetaldehydeacetals and/or crotonaldehyde is reacted with a second educt consisting of formaldehyde and/or formaldehydeacetals and/or hexamethylenetetramine. The reaction is conducted in a liquid, aqueous phase at a temperature of 180° to 280° C. in a closed vessel in the presence of an amide of a carboxylic acid.

6 Claims, No Drawings

PROCESS FOR THE PRODUCTION OF 3-PICOLINE

BACKGROUND OF THIS INVENTION

1. Field Of This Invention

This invention relates to a process for the production of 3-picoline.

2. Prior Art

Pyridine bases represent important intermediate products in the chemical industry, as for example in the case of the production of nicotinic acid or nicotinic acid amide. Various processes are known for the production of pyridine bases.

2-Methyl-5-ethylpyridine is currently produced on an industrial scale in the liquid phase process from acetaldehyde or paraldehyde and ammonia in the presence of the most diverse catalysts, such as, ammonium salts. Small quantities of 2- and 4-picoline are obtained as by-products.

2- and 4-picoline are currently produced in gas phase reactions at temperatures of about 400° C. from acetaldehyde and ammonia with the use of solid bed or fluid bed catalysts on the basis of aluminum silicate.

For the production of pyridine as well as of 3-picoline which gains ever greater importance, at the present time gas phase reactions are used—by the addition of formaldehyde to the acetaldehyde, the formation of 2- and 4-picoline is suppressed in favor of 3-picoline. These reactions also take place in the solid bed or fluid bed with aluminum silicate as a catalyst at temperatures of about 400° C. According to these processes, yields of 3-picoline in the order to magnitude of at most 40 to 44 percent are achieved. Beside that, one obtains large quantities of pyridine with such processes.

It is also known that one may start out with unsaturated aldehydes, such as acrolein or crotonaldehyde, instead of saturated aldehydes. These reactions take place at high temperatures in the gaseous phase; the yields are essentially equal in amount as in the case of when saturated aldehydes are used as starting material.

BROAD DESCRIPTION OF THIS INVENTION

The main object of this invention is to provide a process for producing 3-picoline in high yields, whereby the formation of pyridine is suppressed as much as possible. Other objects and advantages of this invention are set out herein or are obvious to one ordinarily skilled in the art herefrom.

The objects and advantages of this process are achieved by the process of this invention.

This invention involves a process for producing 3-picoline. The process includes reacting a first educt consisting of acetaldehyde and/or at least one acetaldehydeacetal and/or crotonaldehyde with a second educt consisting of formaldehyde and/or at least one formaldehydeacetal and/or hexamethylenetetramine. The reaction is conducted in a liquid, aqueous phase at a temperature of 180° to 280° C. in a closed vessel in the presence of an amide of a carboxylic acid.

The term acetaldehyde, as used within the scope of this invention, includes its polymers, such as, paraldehyde. The term formaldehyde, as used within the scope of this invention, includes its polymers, for example, trioxane.

Preferably the individual possible components of the first and second educts are always only used individually. Thus, the first educt is preferably acetaldehyde or an acetaldehydeacetal or crotonaldehyde, and the second educt is preferably formaldehyde or a formaldehydeacetal or hexamethylenetetramine.

The amides of carboxylic acids which are important for the reaction may be, for example, amides of aliphatic or aromatic of heterocyclic mono- or polycarboxylic acids. Examples of such are the amides of carbonic acid (urea), acetic acid, propionic acid, butyric acid, succinic acid, glutaric acid, adipic acid, benzoic acid, phthalic acid, terephthalic acid or the pyridine carbonic acids, such as, nicotinic acid or isonicotinic acid. The amides of the carboxylic acids are used effectively in quantities of 0.1 to 8 mole, related to the mole-sum of the educts.

For the formation of 3-picoline from acetaldehyde and/or an acetaldehydeacetal and/or crotonaldehyde and formaldehyde and/or a formaldehydeacetal and/or hexamethylenetetramine, it is advantageous to carry out the reaction in the presence of ammonia. Whenever ammonia is used, it can be used in the form of a gas or an aqueous solution.

Whenever liquid starting materials which are not miscible with one another for example, paraldehyde together with aqueous formaldehyde, are used, it is advantageous to use for homogenization small quantities of homogenizing agents, such as, alcohols, cyclic ethers or preferably preformed 3-picoline, or to feed the liquid nonmiscible starting materials into the reactor using a separate pump for each such starting materials.

Using the process of this invention, 3-picoline surprisingly is obtained in good yields and surprisingly the formation of pyridine is strongly suppressed. As by-products, 3-ethylpyridine as well as small quantities of 2,5-dimethylpyridine, 3,5-dimethylpyridine and 2-methyl-5-ethylpyridine are obtained.

The process of this invention is carried out effectively with a mole ratio of acetaldehyde and/or an acetaldehydeacetal to formaldehyde and/or formaldehydeacetals of between 1 to 0.5 and 1 to 1.2, preferably between 1 to 0.8 and 1 to 1.

If crotonaldehyde is used instead of acetaldehyde and/or an acetaldehydeacetal, the mole ratio of crotonaldehyde to formaldehyde and/or a formaldehydeacetal shifts correspondingly to from 1 to 1 to 1 to 2.4.

Whenever hexamethylenetetramine is used in place of formaldehyde and/or a formaldehydeacetal, the mole ratio of acetaldehyde and/or an acetaldehydeacetal to hexamethylenetetramine shifts to from 1 to 0.083 to 1 to 0.2.

The reaction temperature advantageously is 180° to 280° C., quite effectively is from 205° to 240° C., and preferably is from 225° to 235° C.

The reaction is carried out in the liquid phase (aqueous phase) at a pressure which occurs in the case of the reaction in the closed vessel at a predetermined temperature. It is advantageous to stir the reaction batch during the reaction.

The quantity of ammonia used is from 0.5 to 3 mole ammonia per mole of educts, and most effectively is from 0.6 to 1.0 mole per mole of educts.

Effectively, the addition of the aldehyde is accomplished according to the measure of its consumption. Thus, it is favorable for example in the case of operation in a 2-liter container and the use of 350 ml of aldehyde, to add the latter continuously over a 30 to 90 minute period. In the case of different conditions, corresponding addition times are to be selected.

At the end of the desired rotation period, the temperature is lowered to ambient temperature and the 3-picoline is obtained in a known or conventional manner from the reaction mixture. One method involves first bringing the pH value of the water phase into the basic range and then extracting the organic material from the aqueous reaction mixture with an organic solvent, for example, benzene, toluene, xylene, methylene chloride, chloroform, ether and others. The organic solvent is then evaporated and 3-picoline is obtained by fractionated distillation. Within the scope of this invention, any other useful method for the separation and production of the product can be used.

Although this invention had been described as a discontinuous process, the process can also be carried out continuously within the scope of the present invention. In the case of an embodiment of a continuous process, the reaction participants are introduced continuously into a suitable pressure reactor from which the reaction mixture is withdrawn continuously. The reaction products are separated from it, the aqueous phase is concentrated and unchanged reaction participants are then again supplemented and returned into the reaction vessel.

The continuous process can be carried out in any reactor which permits a homogeneous mixing of the reaction participants while stirring vigorously, for example, in a continuously stirred tank reactor.

By way of summary, this invention involves a process for the production of 3-picoline by reacting acetaldehyde and/or an acetaldehydeacetal and/or crotonaldehyde and formaldehyde and/or a formaldehydeacetal and/or hexamethylenetetramine in the liquid phase in the presence of an amide of a carboxylic acid at a temperature of 180° to 280° C. in a closed vessel.

DETAILED DESCRIPTION OF THIS INVENTION

As used herein, all parts, percentages, ratios and proportions are on a weight basis unless otherwise stated herein or otherwise obvious herefrom to one ordinarily skilled in the art.

EXAMPLE 1

1140 ml of an aqueous solution of 134.7 g of acetamide and 50.1 g of ammonia (pH of the solution=11.9) were heated in a 2-liter autoclave to 230° C. and were stirred at 1500 rpm. A mixture of 117.6 of acetaldehyde and 213.3 g of a 30.2% aqueous formaldehyde solution (mole ratio=1 to 0.80) was continuously pumped within a 64 minute period into this solution. At the same time the reaction pressure varied between 34 and 32 bar. After addition of the aldehyde mixture was completed, the reaction mass continued to be stirred for 10 minutes at 230° C. and was then cooled to ambient temperature. Finally, an extraction with 3×100 ml of methylene chloride as well as a gas chromatographic analysis of the united methylene chloride extracts was accomplished. The following products resulted, with the yields related to the acetaldehyde (A) or formaldehyde (F) used: pyridine, 1.3 percent (A); 3-picoline, 57.7 percent (F); 3-ethylpyridine, 15.8 percent (A); 2,5-lutidine, 5.2 percent (A); 3,5-lutidine, 0.7 percent (F); and 2-methyl-5-ethylpyridine, 1.6 percent (A).

All gas chromatographic analyses were carried out with the use of an internal standard as well as with due consideration to surface correction factors.

EXAMPLES 2 TO 7

The procedure for Examples 2 to 7 was the same as in Example 1. The conditions, ingredients, amounts and results of Examples 2 to 7 are set out in the following tables:

TABLE I

| | | Quantity of educt and reaction conditions | | | | | | | |
|---|---|---|---|---|---|---|---|---|---|
| Example No. | Acid Amide | Acid Amide g | $NH_3$ g | pH | $CH_3CHO$ g | $CH_2O$—solution, g | $CH_2O$—content % | duration of dosing minutes | pressure bar |
| 2 | $CH_3CH_2CH_2CONH_2$ | 87.1 | 85.1 | 12.0 | 117,6 | 213.3 | 30.6 | 61 | 41–39 |
| 3 | $(CH_2CONH_2)_2$ | 19.0 | 85.1 | 10.9 | 117,4 | 213.3 | 30.4 | 62 | 42–40 |
| 4 | $PhCONH_2$ | 30.7 | 85.1 | 11.3 | 117,4 | 213.3 | 30.2 | 60 | 38–37 |
| 5 | pyridine-$CONH_2$ | 122.1 | 85.1 | 11.4 | 117,7 | 213.3 | 30.5 | 62 | 38–36 |
| 6 | $NH_2CONH_2$ | 60.1 | 85.1 | 12.5 | 117,4 | 213.3 | 30.6 | 59 | 48–54 |
| 7 | $CH_3CONH_2$ | 229.2 | φ | 5.3 | 117,7 | 213.3 | 30.2 | 66 | 26–28 |

TABLE II

| | Yields, percentages | | | | | |
|---|---|---|---|---|---|---|
| Example No. | pyridine (A) | 3-picoline (F) | 3-ethylpyridine (A) | 2,5-lutidine (A) | 3,5-lutidine (F) | 2-methyl-5-ethylpyridine (A) |
| 2 | 1.5 | 55.4 | 14.7 | 5.4 | 1.0 | 1.5 |
| 3 | 2.1 | 49.8 | 12.0 | 5.5 | 1.4 | 1.4 |
| 4 | 1.9 | 47.3 | 11.5 | 5.1 | 1.3 | 1.3 |
| 5 | 1.8 | 55.9 | 13.8 | 5.2 | 0.9 | 1.5 |
| 6 | 1.7 | 52.1 | 14.4 | 4.7 | 1.4 | 1.4 |

TABLE II-continued

| Example No. |  (A) |  (F) |  (A) |  (A) |  (F) |  (A) |
| --- | --- | --- | --- | --- | --- | --- |
| 7 | 1.3 | 52.7 | 15.2 | 4.5 | 0.8 | 2.0 |

What is claimed is:

1. Process for the production of 3-picoline characterized in that a first educt consisting of acetaldehyde and/or at least one acetaldehydeacetal and/or crotonaldehyde is reacted with a second educt consisting of formaldehyde and/or at least one formaldehydeacetal and/or hexamethylenetetramine in a liquid, aqueous phase at a temperature of 180° to 280° C. in a closed vessel in the presence of an amide of a carboxylic acid.

2. Process as claimed in claim 1 wherein acetaldehyde, as such or in the form of one of its derivatives, and formaldehyde, as such or in the form of one of its derivatives, are used in a molar ratio of from 1 to 0.5 to 1 to 1.2.

3. Process as claimed in claim 1 or 2 wherein the reaction is carried out in the presence of ammonia.

4. Process as claimed in claim 1 wherein the reaction is carried out at a temperature of 205° to 240° C.

5. Process as claimed in claim 1 wherein the carboxylic acid amide is used in a quantity of 0.1 to 8 mole, related to the mole sum of the educts.

6. Process as claimed in claim 1 wherein the carboxylic acid amide is an amide of an aliphatic or aromatic or heterocyclic monocarboxylic acid or polycarboxylic acid.

* * * * *